United States Patent [19]
Yamada et al.

[11] Patent Number: 5,213,579
[45] Date of Patent: May 25, 1993

[54] INTRAOCULAR LENS HAVING BALLOON MEMBER AND TUBE FILLED WITH GEL

[75] Inventors: Yoshiharu Yamada, Toyota; Yuriko Mizumoto, Nagoya, both of Japan

[73] Assignee: Menicon Co, Ltd., Japan

[21] Appl. No.: 808,897

[22] Filed: Dec. 18, 1991

[30] Foreign Application Priority Data

Dec. 25, 1990 [JP] Japan ................... 2-414545

[51] Int. Cl.$^5$ ............................... A61F 2/16
[52] U.S. Cl. ............................. 623/6; 623/11
[58] Field of Search ........................ 623/6, 11

[56] References Cited

U.S. PATENT DOCUMENTS

| | | | |
|---|---|---|---|
| 4,373,218 | 2/1983 | Schachar | 623/6 |
| 4,585,457 | 4/1986 | Kalb | 623/6 |
| 4,822,360 | 4/1989 | Deacon | 623/6 |
| 4,907,592 | 3/1990 | Harper | 128/419 P |
| 5,035,710 | 7/1991 | Nakada et al. | 623/6 |

FOREIGN PATENT DOCUMENTS

| | | |
|---|---|---|
| 0293560 | 12/1988 | European Pat. Off. . |
| 0328117 | 8/1989 | European Pat. Off. ............ 623/6 |
| 63-200755 | 8/1988 | Japan . |
| 64-32859 | 2/1989 | Japan . |
| 1-227753 | 9/1989 | Japan . |

*Primary Examiner*—Ronald Frinks

[57] ABSTRACT

An intraocular lens including a balloon member formed of an elastomer and adapted to be inserted into a capsular bag of an eye, an optically transparent fluid which is injected into the balloon member so that the balloon member expands and fills the capsular bag, and a tube provided on the balloon member and having a bore through which the optically transparent fluid is injected into the balloon member. The bore of the tube is filled with and fluid-tightly closed by a gel filler. The fluid serving as a lens medium is injected into the balloon member through the tube, with the gel filler inhibiting leakage of the fluid from the balloon member.

23 Claims, 4 Drawing Sheets

INTRAOCULAR LENS HAVING BALLOON MEMBER AND TUBE FILLED WITH GEL

BACKGROUND OF THE INVENTION

1. Field of the Invention

The present invention relates in general to an intraocular lens having a balloon member. The intraocular lens is filled by injection with a fluid after being inserted into a capsular bag normally containing the natural crystalline lens body (i.e., lens nucleus and lens cortex) of the human eye. More particularly, this invention is concerned with an intraocular lens which is free from leakage of the injected fluid from the balloon member, during and after the injection of the fluid into the lens.

2. Discussion of the Related Art

Intraocular lenses have been used, for example, as a dioptric substitute for rectifying one's eyesight after cataract surgery. Such lenses may be implanted in the anterior or posterior chamber of the eye, or may be supported by the iris. In particular, it is biologically natural and therefore desirable to replace the natural crystalline lens by the posterior chamber lens, that is, to insert such a lens in the capsular bag which has been emptied of the natural crystalline lens body.

Upon implantation of the intraocular lens in the capsular bag, the insertion of the lens in the eye requires the surgeon to make a scleral incision sufficiently large to allow the passage of the lens through the sclera. However, an excessively large incision will cause the patient to suffer from astigmatism after the surgery. Therefore, it is desirable that the intraocular lens is relatively small to allow insertion into the eye through a minimal incision.

To this end, there have been proposed some methods of inserting and fixing an intraocular lens in the capsular bag. For example, U.S. Pat. No. 4,449,257 discloses an intraocular lens made of water absorptive polymer containing hydroxyethyl methacrylate (HEMA). This lens is inserted into the eye while it is dry and small in size, and then expands and softens with uptake of aqueous humor to fill the capsular bag. In this case, the size of the scleral incision which allows the insertion of such a lens can only be reduced to about 4 mm, though it varies depending on the swelling rate of the lens material. Further, the intraocular lens placed in the capsular bag needs to freely expand and contract so as to closely follow the movement of the capsular bag. Preferably, the lens has the same shape as the crystalline lens body originally contained in the capsular bag, and is accommodated in the capsular bag in close contact with the inner surface thereof.

In view of the above situation, the inventors proposed an intraocular lens which consists of a balloon member formed of an elastomer, and an optically transparent fluid adapted to be injected into the balloon member, as disclosed in JP-A-63-200755, JP-A-64-32859 and JP-A-1-227753. The balloon member is inserted into the capsular bag which has been emptied of the crystalline lens body, and is then filled by injection with the transparent fluid so as to expand and fill the capsular bag. Thus, the balloon member filled with the fluid assumes substantially the same configuration as the natural crystalline lens body originally accommodated in the capsular bag.

Upon implantation of the intraocular lens as described above, the balloon member is folded into a compact form with the air or other gas removed from the member, to enable it to be inserted into the capsular bag. This makes it possible to reduce the size of the scleral incision for allowing the passage of the balloon member. Further, the balloon member assumes substantially the same shape as the crystalline lens body after the injection of the fluid, and is therefore properly fixed in position within the capsular bag. The thus obtained intraocular lens is able to closely follow the movement of the capsular bag, so as to adjust one's eyesight in the same manner as the natural lens.

In the intraocular lens as disclosed in JP-A-1-227753, the fluid is injected into the balloon member with use of a catheter, through a hollow tube provided on the balloon member. During the injection, however, the fluid in the balloon member may possibly leak from a clearance between the tube and the catheter. Otherwise, the injected fluid may leak through the tube, when the catheter is pulled out of the tube upon completion of the injection.

To avoid the leakage of the injected fluid, JP-A-63-200755 discloses a check valve formed at an inlet of the balloon member for the injection, while JP-A-64-32859 discloses a self-closure ring member mounted on the balloon member to automatically close or seal the balloon member. However, the check valve is rather complicated in construction, while the ring member need to be formed as a unit with the balloon member, resulting in cumbersome process for forming the lens. Thus, there is still plenty of room for improvement in the conventional intraocular lenses.

SUMMARY OF THE INVENTION

It is therefore an object of the invention to provide an intraocular lens which is considerably simple in construction, and which is substantially free from leakage of fluid from a balloon member while the fluid is injected into the balloon member through a catheter, and when the catheter is pulled out of the balloon member upon completion of the injection.

The above object may be attained according the principle of the present invention, which provides an intraocular lens comprising: (a) a balloon member formed of an elastomer and adapted to be inserted into a capsular bag in an eye; (b) an optically transparent fluid which is injected into the balloon member so that the balloon member expands and fills the capsular bag; (c) a tube provided on the balloon member and having a bore through which the optically transparent fluid is injected into the balloon member; and (d) a gel filler filling and fluid-tightly closing the bore of the tube, the optically transparent fluid being injected into the balloon member through the tube, with the gel filler inhibiting leakage of the fluid from the balloon member.

The intraocular lens of the present invention constructed as described above is suitably used as a dioptric substitute for rectifying one's eyesight after cataract surgery. More specifically, the balloon member formed of an elastomer can be folded into a compact form, and inserted into the capsular bag, through relatively small incisions formed through the sclera and the capsular bag. Since the final configuration of the balloon member substantially corresponds to the shape of the natural crystalline lens body of the eye, the balloon member is held in close contact with the inner surface of the capsular bag upon injection of the fluid. Further, the intraocular lens of the invention closely follows the movement of the capsular bag, so as to adjust one's eyesight in the same manner as the natural lens, and thus serves effectively as an artificial crystalline lens.

Further, the present intraocular lens with the tube filled with the gel filler is considerably simple in construction, and is advantageously free from leakage of the fluid during injection of the fluid into the balloon member, due to the self-closure property of the gel filler. Upon completion of the injection, a catheter used for injecting the fluid is pulled out of the balloon member without any leakage of the fluid from the balloon member.

BRIEF DESCRIPTION OF THE DRAWINGS

The above and optional objects, features and advantages of the invention will be better understood by reading the following description of one presently preferred embodiment of the invention, when considered in conjunction with the accompanying drawings, in which.

DETAILED DESCRIPTION OF THE PREFERRED EMBODIMENT

Figure 1:
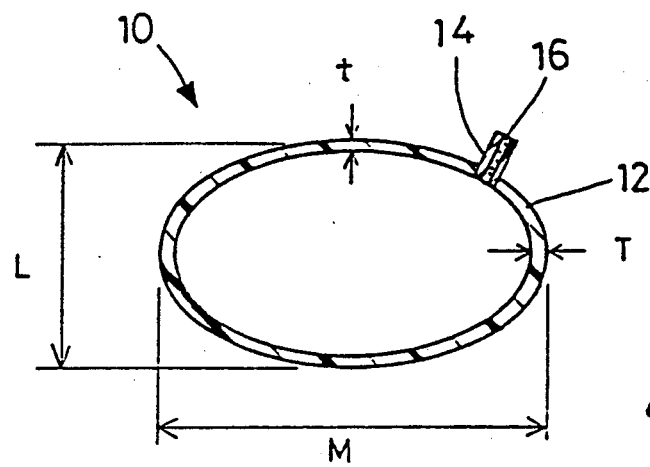
FIG. 1 is a cross sectional view of one embodiment of an intraocular lens constructed according to the present invention.
Figure 6:
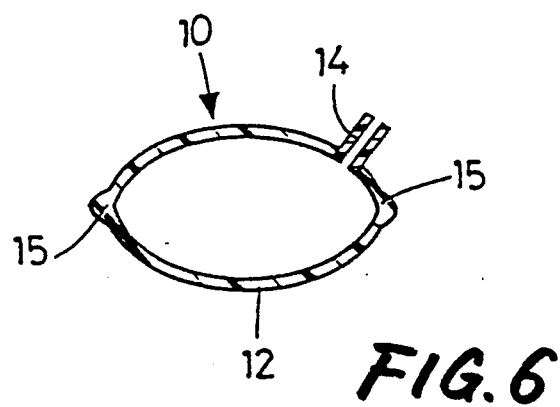
FIG. 6 is a cross sectional view of another form of a balloon member used for the intraocular lens of the present invention.

Referring first to FIG. 1, there is illustrated a lens system 10 as one preferred embodiment of an intraocular lens constructed according to the present invention. The lens system 10 consists of a hollow balloon member 12, and a tube 14 which protrudes a suitable length from the balloon member 12. The tube 14 has a bore which communicates with the interior of the balloon member 12 and the exterior space, and which is filled with a gel filler 16. The balloon member 12 is formed of an elastomer, and assumes a shape substantially following the original shape of a capsular bag normally containing the natural crystalline lens body (i.e., lens nucleus and lens cortex) of the human eye. Preferably, the balloon member 12 is formed into a biconvex shape having no protrusions formed on its periphery, as shown in FIG. 1. It is to be understood that thick-walled portions 1,5 shown in FIG. 6 should not be considered as protrusions. Thus, the balloon member 12 is advantageously formed as an integral hollow member having a biconvex shape, as shown in FIG. 1.

The balloon member 12 of the lens system 10 is inserted into the capsular bag which has been emptied of the crystalline lens body, and a suitable fluid as a lens medium is injected into the balloon member 12 so that the member 12 is inflated to fill the capsular bag. It is therefore desirable that the elongation of the balloon member 12 is equal to or higher than about 50%. Since the balloon member 12 cooperates with the injected fluid to function as an artificial crystalline lens, the balloon member 12 is generally formed of an optically transparent material having at least 65% of visible light transmittance (i.e., transmittance with respect to light in a frequency range of 380–780 nm). Further, it is desirable to form the balloon member 12 of a fluid impervious material so as to prevent the injected fluid from leaking out into the eye, and to prevent minute contents in aqueous humor from being deposited in the material of the balloon member 12.

To satisfy the above requirements, the material for the balloon member 12 may be advantageously selected from polyurethane, silicone rubber, segmented polyurethane, a block- or graft-copolymer of polysiloxane and polyurethane, and other materials. To the selected material of the balloon member 12, there may be added as needed various known additives, such as a dye and an ultraviolet ray absorbent agent.

The balloon member 12 is formed into substantially the same configuration as the crystalline lens body of the human eye, as shown in FIG. 1. With a fluid injected into the interior of the balloon member 12, therefore, the member 12 is favorably retained in position within the capsular bag such that the outer surface of the member 12 is held in close contact with the inner surface of the capsular bag.

While the dimensions of the balloon member 12 may be suitably determined as desired, it is preferable that its diameter M (FIG. 1) is int he range between about 6 mm and about 13 mm, while its thickness L (FIG. 1) is in the range between about 2 mm and about 6 mm. The balloon member 12 having such dimensions has almost the same diameter and thickness as the capsular bag, when the member 12 is inserted into the capsular bag and is filled by injection with the fluid.

The balloon member 12 has a radially inner optically effective portion (i.e., a generally central portion through which light is transmitted), which has a considerably small wall thickness t (FIG. 1) of about 0.001 mm to about 0.1 mm, preferably, about 0.005 mm to about 0.05 mm. Accordingly, the balloon member 12, when it is deflated, may be folded into a compact form to enable it to be inserted into the capsular bag through a comparatively small incision.

The biconvex balloon member 12 further has an outer peripheral portion whose wall thickness T (FIG. 1) is in the range between about 0.05 and about 1.0 mm, preferably, 0.1–0.5 mm. More preferably, the wall thickness T is made slightly larger than the wall thickness t of the optically effective portion indicated above, so that the final lens configuration after the injection of the fluid is kept to be identical with that of the removed natural crystalline lens body.

While the tube 14 fixed to the balloon member 12 may be formed of a non-transparent material, the tube 14 is desirably formed of a transparent material so as to minimize unfavorable influence on an optical portion (within the range of the pupil) of the lens system 10. Additionally, the tube 14 is desirably formed of a relatively flexible material, in view of mechanical stress or burden on the capsular bag, and handling ease upon injection of the fluid into the balloon member 12. More specifically, the material for the tube 14 may be selected from: the above-indicated materials used for the balloon member 12; silicone; polyurethane; polyvinyl chloride; polyester; elastomers such as fluororubber; polyolefine such as thin-walled polypropylene; and fluorocarbon polymer such as polytetrafluoroethylene. The tube 14 may be formed integrally with the balloon member 12, or may be formed separately from the balloon member 12, and then bonded to an opening formed through the member 12.

Figure 2:
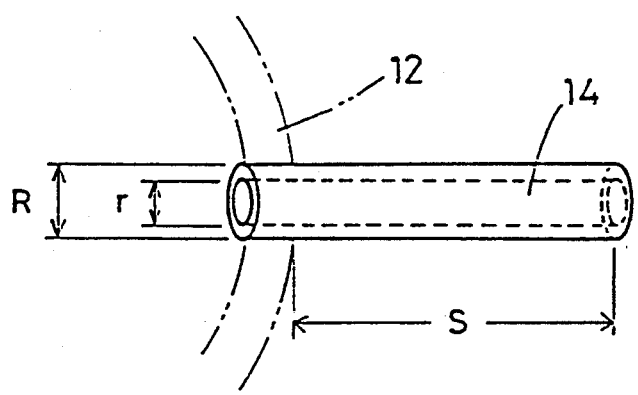
FIG. 2 is a perspective view showing a tube formed as a part of the intraocular lens of FIG. 1.

The tube 14 has an outside diameter R (FIG. 2) of about 2 mm or smaller, preferably, about 1 mm or smaller, in view of handling ease upon the insertion of the lens system 10 into the capsular bag or upon the injection of the fluid into the balloon member 12. To facilitate the injection of the fluid into the balloon member 12, the inside diameter r (FIG. 2) of the tube 14 is set to be about 0.05 mm or larger, preferably, about 0.1 mm or larger. Further, the length S of protrusion of the tube 14 as measured from the outer surface of the balloon member 12 is set to be about 2 mm or larger, preferably about 3 mm or larger, so as to facilitate the injection of the fluid from the outside of the capsular bag into the balloon member 12. The tube 14 whose inner axial end portion protrudes excessively into the balloon member 12 will affect the patient's eyesight, and make it difficult to remove the residual air from the balloon member 12 after injection of the fluid. Accordingly, the tube 14 is preferably fixed to the balloon member 12 such that the axial end of the tube 14 lies in substantially the same plane with the inner surface of the balloon member 12, as shown in FIG. 2.

The tube 14 is preferably mounted on the front side of the balloon member 12, because of handling ease upon injection of the fluid into the balloon member 12, and the tendency of the residual air to be left in the upper portion (the front side) of the balloon member 12 during a lens implanting operation. It is also preferable that the tube 14 is mounted radially outwardly of the optically effective portion of the balloon member 12, in view of unfavorable influence on the patient's eyesight. Preferably, the tube 14 is spaced at least 1.5 mm, more preferably at least 2 mm, radially outwards from the center of the balloon member 12.

According to the present invention, the bore of the tube 14 is filled with and closed by the gel filler 16. When a catheter, for example, is inserted through the tube 14 in order to inject the fluid into the balloon member 12, the injected fluid is not allowed to pass through the tube 14 due to the presence of the gel filler 16 filling the space between the catheter and the tube 14. When the catheter is then pulled out of the tube 14, the bore of the tube 14 is spontaneously closed due to the auto-sealing property of the gel filler 16. Namely, the filling of the tube 14 with the filler 16 is effective to eliminate leakage of the injected fluid out of the balloon member 12, during and after injection of the fluid through the catheter, for example.

The gel filler 16 is prepared from a liquid precursor whose viscosity is about 300,000 centipoise or lower, so that the gel precursor can be easily injected into the tube 14 to fill the bore. After gelation of the injected precursor, the gel filler 16 is adapted to fluid-tightly close the bore of the tube 14 due to its auto-sealing property. To assure a sufficient degree of auto-sealing property, the gel filler 16 must be elastic, desirably having elongation of at least 100%, and penetration index of at least 40 when measured by using a micro consistency (coned) needle having ¼ inch in length according to JIS-K-2207, which corresponds to ASTM D5.

While the gel filler 16 may be transparent or non-transparent, like the material for the tube 14, it is preferable to make the gel filler 16 of a transparent material so as to minimize unfavorable influence on the optical portion (within the range of the pupil) of the lens system 10. Further, the gel filler 16 is desirably retained in the tube 14 due to its chemical or physical connection, for example, so that the filler 16 does not fall out of the tube 14 when an injector or a catheter is inserted into the tube 14 filled with the gel filler 16.

It is to be understood that there is no limitation in components of the gel precursor and the manner of forming a gel from the precursor. It is possible to employ various known components which have been conventionally injected into the balloon member 12 to form a gel, and various known manners of forming a gel from such components, as disclosed in U.S. Pat. No. 5,116,369, JP-A-2-109568 and JP-A-2-255151, for example.

It is also possible to form a gel by heating addition hardening type silicone as a gel precursor to cause addition reaction thereof. Acrylamide may be formed into a relatively hard gel by addition of a crosslinking agent (such as N,N'-methylene-bis-acrylamide, N,N'-bis-acyl cystamin) and a polymerization promoter (such as ammonium peroxodisulfate, N,N,N',N'-tetramethyl ethylene diamine), and subsequent free radical addition reaction thereof. Agarose may be dissolved in hot water to provide an at least 1% agarose solution, which is then cooled to 40° C. or lower to form a gel. Similarly, gelatin may be dissolved in hot water to provide an at least 2-3% gelatin solution, which is then cooled to 40° C. or lower to form a gel by intermolecular aggregation. Gelatin may also be formed into a relatively hard gel, by addition of formalin which gives rise to crosslinking between amino groups of molecules. Further, an acid collagen solution whose pH value is made around neutrality is provided with salt (NaCl), and then kept at 25-37° C., whereby collagen molecules aggregate to form a gel.

The amount of injection of the gel precursor as described above is equal to the amount of the gel filler 16 filling the tube 14. Since a protruding portion of the tube 14 is cut off after injection of the fluid into the balloon member 12, the gel precursor (gel filler 16) needs to fill at least a portion of the tube 14 which is located in the opening of the balloon member 12.

Figure 3:
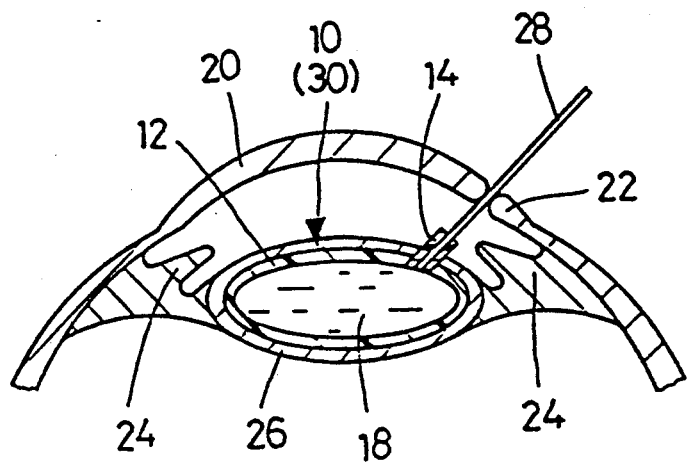
FIG. 3 is a cross sectional view showing the present intraocular lens implanted in the eye, with a catheter inserted through the tube for injection of a fluid into a balloon member.
Figure 4:
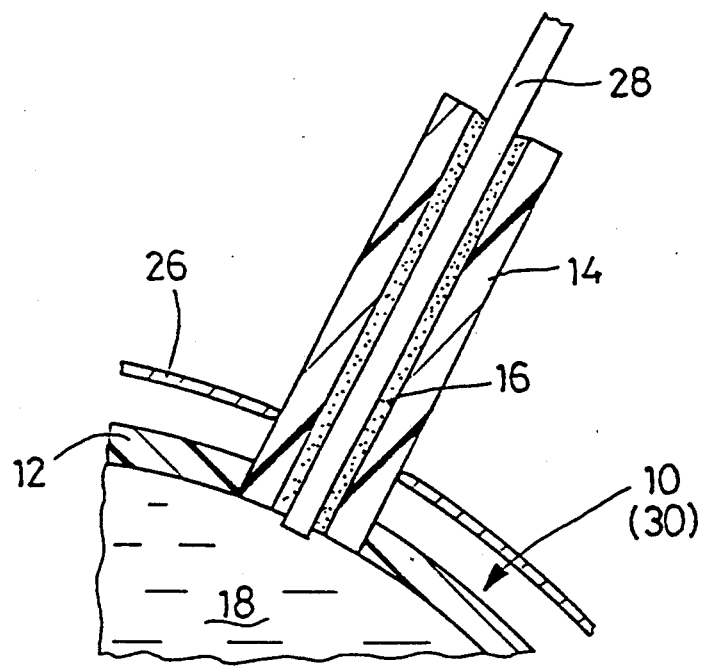
FIG. 4 is an enlarged view showing in detail the tube of the intraocular lens together with the catheter.
Figure 5:
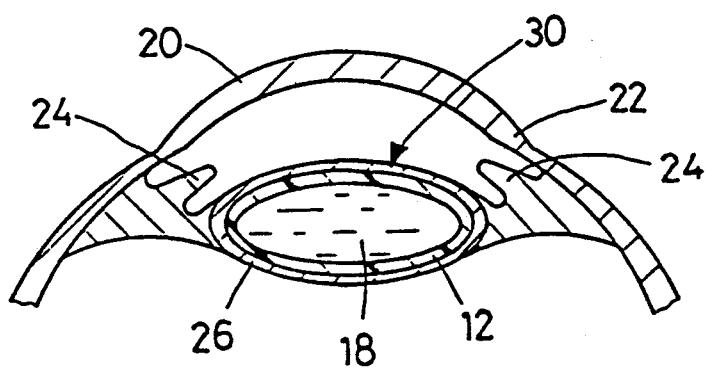
FIG. 5 is a cross sectional view showing the intraocular lens of the invention when placed in the capsular bag normally containing the crystalline lens body of the eye.

Referring next to FIGS. 3 through 5, there will be described the manner of inserting the thus constructed lens system 10 into the human eye, and positioning the lens system 10 in the capsular bag of the crystalline lens, so as to permit it to function as an intraocular lens which replaces the crystalline lens.

Referring to FIG. 3 which shows a portion of the eye in cross section, the natural crystalline lens body of the cataract is surgically removed from the capsular bag 26, through a minimal incision formed through a portion of the sclera 22 around the cornea 20, without damaging the iris and other tissues. On the other hand, the bore of the tube 14 fixed to the balloon member 12 of the lens system 10 is filled with a given gel precursor, which is heated or otherwise treated to form a gel, so that the bore is closed by the obtained gel filler 16. The gas or air in the balloon member 12 is sucked and removed with a catheter 28, for example, inserted through the tube 14, before or after filling of the tube 14 with the gel filler 16. Thus, the balloon member 12 is deflated and reduced in size. Since the gel filler 16 filling the bore of the tube 14 serves as a plug for fluid-tightly closing the balloon member 12, the air is prevented from flowing through the tube 14 back into the balloon member 12, whereby the balloon member 14 is kept in reduced size and can be folded into a compact form. In this condition, the balloon member 12 can be inserted into the capsular bag 26, through the minimal incisions formed through the sclera 22 and the capsular bag 26. Thus, the lens system 10 is easily inserted into the capsular bag 26, with a suitable means such as a catheter 28.

During the insertion of the lens system 10, the catheter 28 is favorably attached to the balloon member 12 by way of the tube 14, and is prevented from slipping out of the tube 14 due to the gel filler 16, assuring improved handling ease upon insertion of the lens system 10 into the capsular bag 26. It is also possible to insert the lens system 10 into the capsular bag 26 by means of the tube 14 having a suitable length, without using the catheter 28, through a small incision which has been made upon removal of the crystalline lens body.

Subsequently, the fluid 18 is injected through the catheter 28 in the tube 14, into the interior of the balloon member 12, as shown in FIG. 3. Thus, the balloon member 12 is filled with the fluid 18, and is inflated to be in close contact with the inner surface of the capsular bag 26, to thereby provide an intraocular lens 30 which is securely held in place in the capsular bag.

The injection 18 in the balloon member 12 is adapted to inflate the balloon member 12 to enable it to fill the capsular bag 26, to thereby provide the intraocular lens 30 which serves as the crystalline lens. Therefore, the injection 18 is desirably a light-transmitting fluid, in particular, a transparent liquid, which has a refractive index of at least 1.36, and a viscosity of about 300,000 centipoise or smaller, permitting it to be easily injected into the balloon member 12.

More specifically, the injection or fluid 18 in the balloon member 12 may be selected from: a solution or a crosslinked gel of polysaccharide or derivatives thereof, such as cellulose, chitin, alginic acid, and hyaluronic acid; a solution of synthetic polymer electrolyte such as polyacrylic acid, polyacrylamide propylsulfonic acid, and polystyrene sulfonic acid; a solution of water-soluble oligomer such as hydroxy ethyl methacrylate, N-vinyl pyrrolidone, and polyvinyl alcohol; silicone oil; and silicone gel. However, the fluid 18 is by no means limited to those indicated above. The fluid 18 preferably takes the form of a gel after injection, since the fluid 18 before gelation may be easily injected into the balloon member 12, and the fluid 18 after gelation is unlikely to leak out of the member 12. The amount of the injected fluid 18 is determined so as to fill the volume of the capsular bag, generally, in the range between about 0.1 and about 0.8 ml.

In the lens system 10 of the present invention, there arises no clearance between the tube 14 filled with the gel filler 16, and the catheter 28 inserted through the tube 14, as shown in detail in FIG. 4. Accordingly, the leakage of the fluid 18 is effectively avoided during the injection of the fluid 18 into the balloon member 12. After a slight amount of the residual air or gas in the balloon member 12 is sucked through the catheter 28, and thus completely removed, the catheter 28 is pulled out of the balloon member 12 (tube 14). During this operation, too, the leakage of the fluid 18 is effectively avoided since the bore of the tube 14 remains fluid-tightly closed due to the self-sealing property of the gel filler 16. Thus, the lens system 10 of the invention is free from leakage of the fluid 18 during the injection, and when the catheter 28 is pulled out upon completion of the injection.

Upon completion of the injecting operation as described above, a portion of the tube 14 (which protrudes from the balloon member 12) is cut off by scissors, heat or a laser, for example. To more surely avoid the leakage of the fluid 18, it is possible to plug the tube 14 with a rod, for example, fitted in the tube 14, or by melting and sealing the tube 14 by means of a laser, for example. Where the fluid 18 consists of a material (e.g., polymerized silicone) which can be rapidly polymerized after injection, there is no need to seal the tube 14, in view of unlikelihood of leakage of the fluid 18 from the balloon member 12.

The implantation of the intraocular lens 30 is accomplished by suturing the incision in the sclera, as shown in FIG. 5. Thus, the intraocular lens 30 is held in close contact with the entire inner surface of the capsular bag 26, and fixed in place in the eye. In addition, the lens 30 is able to closely follow the movement of the capsular bag, because of relatively small wall thickness of the balloon member 12, and thus serves excellently as an artificial crystalline lens which is able to adjust one's eyesight in the same manner as the natural crystalline lens.

Figure 7:
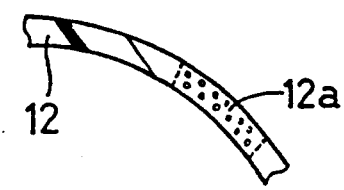
FIG. 7 is an enlarged view showing an air permeable film provided in the intraocular lens of FIG. 1.

The lens system 10 of the present invention may be provided with an air-permeable film 12a as shown in FIG. 7, which allows the passage of the air therethrough but inhibits the passage of the fluid 18 therethrouth, so that the air may be removed from the balloon member 12 through the film 12a. The air-permeable film 12a may be a hydrophobic porous film such as a fluororesin film, polyolefin, and fluorocarbon, or may take the form of a thin film consisting of a bundle of hollow fibers. Air-permeable film 12a may be formed integrally with the balloon member 12, or may be formed separately from the member 12 and attached thereto afterwards. The diameter of the air-permeable film 12a is preferably not larger than about 4 mm. Like the tube 14, the film 12a is desirably provided on the front side of the balloon member 12, at its portion which is spaced at least 1.5 mm, preferably at least 2 mm, radially outwardly of the center of the balloon member 12.

With the air-permeable film 12a disposed or exposed outside of the capsular bag 26 during the injection of the fluid 18, it is possible to exhaust the balloon member 12 of the residual air or other gas to the full extent, while avoiding leakage of the fluid 18. Thus, the provision of the film 12a advantageously eliminates an optical problem resulting from bubbles remaining in the fluid 18. Further, there is no need to completely evacuate the balloon member 12 before the lens system 10 is inserted into the capsule bag 26. Accordingly, the operation for evacuating the balloon member 12 prior to the insertion of the lens system 10 can be advantageously simplified.

While the present invention has been described in detail in its presently preferred embodiment, for illustrative purpose only, it is to be understood that the invention is by no means limited to the details of the illustrated embodiment, but may be otherwise embodied with various other changes, modifications and improvements which may occur to those skilled in the art, without departing from the scope of the present invention.

There will be hereinafter described some examples of the present invention, together with the result of measurement on leakage of an injected fluid from each example of intraocular lens.

EXAMPLE 1

To a silicone balloon member, there was attached a silicone tube (available from Dow Corning Corp., U.S.A.) having an outside diameter of 0.64 mm, an insider diameter of 0.30 mm, and a substantially round cross section. After the air in the balloon member was sucked and removed with a catheter inserted into a bore of the tube, addition hardening type silicone ("KE-1052" available from Shin-Etsu Chemical Co., Ltd.) was injected with the catheter into the bore of the tube. Thereafter, an electric heater was contacted with the tube, to heat the silicone in the tube to form a gel due to its thermal hardening reaction. As a result, the bore of the tube was filled with and closed by the thus obtained gel filler. A precursor for the gel filler had a viscosity of 1000 centipoise before gelation, while the gel filler after gelation had a penetration index of 65 when measured by using a micro consistency (coned) needle having $\frac{1}{4}$ inch in length according to JIS-K-2207.

Subsequently, the catheter was inserted through the tube filled with the gel filler, and the addition hardening type silicone as indicated above was injected as a fluid into the balloon member. During the injection of the fluid, and after the catheter was pulled out of the tube, no leakage of the injected fluid from the balloon member was recognized. After a slight amount of the air remaining in the balloon member was sucked and removed with the catheter, the balloon member was fully filled with the injected fluid with no leakage of the fluid from the balloon member.

EXAMPLE 2

50 parts by weight of an ultraviolet-ray-hardening adhesive containing silicone ["X-31-738" available from Shin-Etsu Chemical Co., Ltd.) was mixed with 50 parts by weight of silicone oil ("OF-38G" available from Shin-Etsu Chemical Co., Ltd.) which serves as a hardness adjusting component, and 0.2 parts by weight of camphorquinone which serves as a photopolymerization initiator, so as to prepare a gel precursor having a viscosity of about 1600 centipoise. The thus obtained gel precursor was injected to fill a silicone tube (available from Dow Corning Corp., U.S.A.) having an outside diameter of 0.64 mm, an inside diameter of 0.30 mm, and a substantially round cross section, and was exposed to a halogen lamp (available from Phillips: 15 V, 150 W) for 20 minutes, to form a gel for filling the tube.

Subsequently, the tube was attached to the balloon member, and the air in the balloon member was sucked and removed with a catheter inserted through the tube. Then, a silicone gel ("two liquid type RTV silicone: KE1052" available from Shin-Etsu Chemical Co., Ltd.) was injected with the catheter into the balloon member, and the catheter was then pulled out of the tube. No leakage of the silicone gel was recognized.

What is claimed is:

1. An intraocular lens comprising:
   a balloon member formed of an elastomer and adapted to be inserted into a capsular bag of an eye;
   an optically transparent fluid which is injected into the balloon member so that the balloon member expands and fills the capsular bag;
   a tube provided on the balloon member and having a bore through which the optically transparent fluid is injected into the balloon member; and
   a gel filler filling and fluid-tightly closing the bore of the tube prior to injecting the optically transparent fluid, the optically transparent fluid being injected into the balloon member through the tube, with the gel filler inhibiting leakage of the fluid from the balloon member.

2. An intraocular lens according to claim 1, wherein said balloon member has a biconvex shape after injection of the optically transparent fluid.

3. An intraocular lens according to claim 1, wherein said balloon member has an elongation of not lower than 50%.

4. An intraocular lens according to claim 1, wherein said balloon member is formed of an optically transparent material having at least 65% of visible light transmittance.

5. An intraocular lens according to claim 1, wherein said balloon member is formed of a fluid impervious material.

6. An intraocular lens according to claim 1, wherein said balloon member is formed of a material selected from the group consisting of polyurethane, silicone rubber, segmented polyurethane, and a block- or graft-copolymer of polysiloxane and polyurethane.

7. An intraocular lens according to claim 1, wherein said balloon member has a diameter in the range of 6–13 mm, and a thickness in the range of 2–6 mm.

8. An intraocular lens according to claim 1, wherein said balloon member has a radially inner optically effective portion having a wall thickness of 0.001–0.1 mm.

9. An intraocular lens according to claim 8, wherein said balloon member has an outer peripheral portion located radially outwardly of said optically effective portion, said outer peripheral portion having a wall thickness of 0.05–1.0 mm.

10. An intraocular lens according to claim 9, wherein the wall thickness of said outer peripheral portion of said balloon member is larger than that of said radially inner optically effective portion.

11. An intraocular lens according to claim 1, wherein said tube is formed of a material selected from the group consisting of: polyurethane; silicone rubber; segmented polyurethane; a block- or graft-copolymer of polysiloxane and polyurethane; silicone; polyvinyl chloride; polyester; and elastomers including fluororubber; polyolefine including thin-walled polypropylene; and fluorocarbon polymer including polytetrafluoroethylene.

12. An intraocular lens according to claim 1, wherein said tube has an outside diameter of not larger than 2 mm, and an inside diameter of not smaller than 0.05 mm.

13. An intraocular lens according to claim 12, wherein the outside diameter of said tube is not larger than 1 mm, and the inside diameter of said tube is not smaller than 0.1 mm.

14. An intraocular lens according to claim 1, wherein said tube protrudes at least 2 mm from an outer surface of said balloon member.

15. An intraocular lens according to claim 1, wherein said tube has an axial end portion fixed to said balloon member, said axial end portion having an axial end face lying in the same plane with an inner surface of said balloon member.

16. An intraocular lens according to claim 1, wherein said tube is spaced at least 1.5 mm radially outwards from the center of said balloon member.

17. An intraocular lens according to claim 1, wherein said gel filler is prepared from a liquid precursor whose viscosity is not higher than 300,000 centipoise.

18. An intraocular lens according to claim 1, wherein said gel filler has an elongation of at least 100%.

19. An intraocular lens according to claim 1, wherein said gel filler has a penetration index of at least 40.

20. An intraocular lens according to claim 1, wherein said optically transparent fluid has a refractive index of at least 1.36, and a viscosity of not larger than 300,000 centipoise.

21. An intraocular lens according to claim 1, wherein said optically transparent fluid is selected from the group consisting of: a solution or a crosslinked gel of polysaccharide and derivatives thereof including cellulose, chitin, alginic acid, and hyaluronic acid, and derivatives thereof; a solution of synthetic polymer electrolyte including polyacrylic acid, polyacrylamide propylsulfonic acid, and polystyrene sulfonic acid; a solution of water-soluble oligomer including hydroxyethyl methacrylate, N-vinyl pyrrolidone, and polyvinyl alcohol; silicone oil; and silicone gel.

22. An intraocular lens according to claim 1, wherein the amount of said optically transparent fluid injected into said balloon member is in the range of 0.1–0.8 ml.

23. An intraocular lens according to claim 1, further comprising an air-permeable film provided on said balloon member, said air-permeable film allowing the passage of the air therethrough while inhibiting the passage of said optically transparent fluid therethrough.

* * * * *